United States Patent [19]

Wise et al.

[11] Patent Number: 5,407,916

[45] Date of Patent: Apr. 18, 1995

[54] NEUROTENSIN MIMETICS AS CENTRAL NERVOUS SYSTEM AGENTS

[75] Inventors: Lawrence D. Wise; David J. Wustrow, both of Ann Arbor, Mich.

[73] Assignee: Warner-Lambert Company, Morris Plain, N.J.

[21] Appl. No.: 159,617

[22] Filed: Dec. 3, 1993

Related U.S. Application Data

[63] Continuation-in-part of Ser. No. 17,556, Feb. 16, 1993, abandoned.

[51] Int. Cl.⁶ .................... A61K 37/00; A61K 37/02; C07K 5/00; C07K 7/00
[52] U.S. Cl. ..................................... 514/17; 514/18; 530/329; 530/330
[58] Field of Search ................... 514/17, 18; 530/329, 530/330

[56] References Cited

FOREIGN PATENT DOCUMENTS 0333071 9/1989 European Pat. Off. .

OTHER PUBLICATIONS

McLean et al. Pharm. Biochem. Behavior vol. 8 p. 97 (1978).
Poster: Tsuchiya Y, et al. Presented at 200th American Chemical Society Meeting Washington, D.C. 1990 Abstract MEDI0015.
European Journal of Pharmacology, Lugrin D., et al. 1991; 205:191–98.
European Journal of Pharmacology, Dubuc I, et al. 1992;219:327–9.

*Primary Examiner*—Jill A. Warden
*Assistant Examiner*—Sheela J. Huff
*Attorney, Agent, or Firm*—Francis J. Tinney

[57] ABSTRACT

Neurotensin mimetics are described, as well as methods for the preparation and pharmaceutical composition of same, which are useful as central nervous system agents and are particularly useful as analgesic and antipsychotic agents.

6 Claims, No Drawings

NEUROTENSIN MIMETICS AS CENTRAL NERVOUS SYSTEM AGENTS

This is a continuation-in-part application of United States Ser. No. 08/017,556, filed Feb. 16, 1993, now abandoned.

BACKGROUND OF THE INVENTION

The present invention relates to novel neurotensin mimetics useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are analgesics and are also useful as antipsychotic agents for treating psychoses such as schizophrenia.

Neurotensin (NT), an endogenous tridecapeptide found in the central nervous system (CNS), has been postulated to be a neurotransmitter or neuromodulator. A wide range of pharmacological effects have been attributed to NT. Two important aspects of NT actions on the CNS are its possible involvement in the etiology of schizophrenia (Nemeroff C, et al, *Neuropsychopharm* 1991;4:27 and its analgesic properties (Clineschmidt BJ, et al, *European Journal of Pharmacology* 1979;54:129–159). Thus, it has been suggested that NT may have neuroleptic-like activity within the CNS. Garver DL, et al, *Am J Psychiatry* 1991;148:484–8 reported data that showed diminished availability of NT in some psychotic patients with increases in neurotensin early in neuroleptic treatment. These results suggest that a NT agonist would be useful as an antipsychotic agent.

Furthermore, Clineschmidt BJ, et al, *European Journal of Pharmacology* 1979;54:129–139 reported an analgesic effect when NT was administered intracisternally to rodents. These results suggest that a NT agonist would be useful as an analgesic agent.

The C-terminal hexapeptide fragment of NT (NT(8–13)) has been shown to retain much of the activity found in the native peptide. Indeed, NT or NT(8–13) have been shown to possess activity in preclinical antinociceptive tests and in animal behavioral tests predictive of antipsychotic efficacy (Ervin G, et al, *Nature* 1981;29:73–76). NT(8–13) is metabolically unstable and this would limit its use as a therapeutic agent. Studies of the catabolism of NT(8–13) in various brain regions have revealed several key amide bonds which are most susceptible to proteolytic degradation (Davis TP, et al, *Journal of Neurochemistry* 1992;58:608–617). Compounds with sufficient metabolic stability may when administered peripherally remain intact long enough to diffuse or be transported across the blood brain barrier and interact with central NT receptors.

European Published Patent Application EP-0333071 disclosed a series of hexapeptide NT analogs of Formula I $$A\text{-}B\text{-}C\text{-}D\text{-}E\text{-}F\text{-}R^1 \qquad (I)$$

(Seq ID No: 1)

wherein A stands for a group

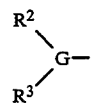

(G stands for a basic amino acid of L- or D-form, and $R^2$ and $R^3$, which may be the same or different, each stands for a hydrogen atom, a lower alkyl group, or an acyl group), a group

(in which G stands for a basic amino acid of L- or D-form, J stands for an amino acid of L- or D-form, and $R^4$ stands for a hydrogen atom or a lower alkyl group), an ω-aminoalkanoyl group

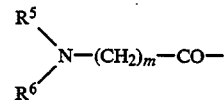

(in which $R^5$ and $R^6$, which may be the same or different, each stands for a-hydrogen atom or a lower alkyl group, and m is an integer of from 1 to 10), or an ω-guanidinoalkanoyl group

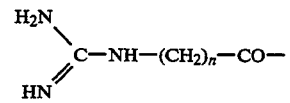

(in which n is an integer of from 1 to 10), or a group having the formula

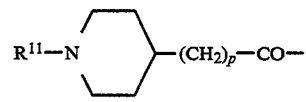

in which $R^{11}$ is hydrogen or a lower alkyl, p is zero or an integer of from 1 to 10, B is a basic amino acid of L-form or an α-N-alkyl derivative thereof, C stands for L-Pro or a derivative thereof, D stands for a natural or nonnatural aromatic amino acid of L-form, E stands for an amino acid of L-form or an α-N-alkyl derivative or α-C-alkyl derivative thereof, F stands for an amino acid of L- or D-form or an α-N-alkyl derivative or α-C-alkyl derivative thereof, and $R^1$ stands for a group

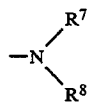

(in which $R^7$ and $R^8$, which may be the same or different, each stands for a hydrogen atom or a lower alkyl group) or a group —O—$R^9$ (in which $R^9$ stands for a hydrogen atom, an alkyl group, an alkenyl group or a group —$(CH_2)_p$—O—$R^{10}$ in which p is an integer of from 1 to 5 and $R^{10}$ stands for an alkyl group, an alkenyl group, or an acyl group).

This series of peptides was purported to be useful as methamphetamine antagonists, antipsychotic agents, cerebral medicaments, and analgesic agents. However, EP-0333071 and a subsequent presentation by Tsuchiya Y, et al, 200th American Chemical Society Meeting, Wash., DC, 1990 Abstract MEDI0015, do not suggest or disclose the compounds of the present invention which contain reduced [ΨCH$_2$NH] amide bond replacements in the 8,9 position of NT(8-13).

Lugrin D, et al, *European Journal of Pharmacology* 1991;205:191-98, disclosed a series of pseudopeptide analogs of neurotensin. They systematically replaced the five peptide bonds in neurotensin (8-13) with CH$_2$NH (Ψ, reduced) bonds. An analog containing the [ΨCH$_2$NH] in the 8,9 position of NT(8-13) (Lys[ΨCH$_2$NH]Lys-Pro-Tyr-Ile-Leu) (Seq ID No: 2) was found to be as potent as NT(8-13).

The compound first disclosed by Lugrin D, et al, in *European Journal of Pharmacology* 1991;205:191-8 was subsequently demonstrated to have analgesic activity when administered directly into the brain, e.g., intracerebral ventricular administration (ICV) (Dubuc I, et al, *European Journal of Pharmacology* 1992;219:327-9). However, there was no disclosure regarding peripheral administration of this compound. We have found that the compound is not active in a behavioral model, a test which is predictive of antipsychotic efficacy (see hereinafter table Biological Activity of Compounds of Formula I). When this compound was tested in two analgesic models, it was completely inactive in the rat tail pressure assay. This assay was carried out according to the modifications outlined in Winder CV, et al, *Archs Int Pharmacodyn Ther* 1959;122:301-11 of the method of Green AF, *Br J Pharmacol* 1951;6:572-87. This test is specific for agents which produce analgesia directly on the CNS. The compound did have weak activity in the acetic acid-induced writhing assay. However, this test, unlike the rat tail pressure assay, is sensitive not only to centrally acting analgesics but additionally anti-inflammatory agents which act in the periphery. We have surprisingly and unexpectedly found, in contrast to the reduced bond analog previously disclosed, the confounds of the present invention have potent activity in both the acetic acid-induced writhing test as well as the rat tail pressure assay indicating they are centrally acting analgesics. Thus, the compounds of the present invention demonstrate a significant advance over the compounds disclosed in EP-0333071 and Lugrin D, et al, *European Journal of Pharmacology* 1991;205:191-8. They represent the first example of 8,9[ΨCH$_2$NH] reduced bond isostere of NT(8-13) which have CNS activity as analgesics or antipsychotic agents when administered peripherally.

Further we have demonstrated that dialkyl amino substituted acetic acids, for example, bis(3-aminopropyl), bis(4-aminobutyl), and bis(3-guanidinylpropyl) substituted acetic acids can serve to replace the Arg-Arg residues in NT (8-13).

SUMMARY OF THE INVENTION

Accordingly, the present invention is a compound of Formula I $$R-CH(-(CH_2)_n-R^1)-CH_2-X-CH(-CH_2-CH_2-CH_2-(CH_2)_{n1}-R^2)-C(=O)-Pro-Trp-Tle-Leu-OR^3 \quad \text{I}$$

(Seq ID No: 3)

wherein
R is H or NH$_2$;
R$^1$ and R$^2$ are each independently NH$_2$ or $$-NH-\overset{NH}{\underset{\|}{C}}-NH_2;$$

R$^3$ is H or lower alkyl;
n is zero or an integer of one to four;
n$^1$ is zero or one;
X is NH or CH$_2$; provided:
when R is H and X is CH$_2$ then R$^1$ and R$^2$ are NH$_2$, n is zero or an integer of one to four, and n$^1$ is zero or one;
when R is NH$_2$ and X is CH$_2$ then R$^1$ is NH$_2$ or $$-NH-\overset{NH}{\underset{\|}{C}}-NH_2,$$

R$^2$ is NH$_2$, n is three or four, and n$^1$ is zero or one;
when R is H and X is NH then R$^1$ is NH$_2$, R$^2$ is NH$_2$ or $$-NH-\overset{NH}{\underset{\|}{C}}-NH_2,$$

n is zero or an integer of one to four and n$^1$ is zero or one;
when R is NH$_2$ and X is NH then R$^1$ and R$^2$ are NH$_2$ or $$-NH-\overset{NH}{\underset{\|}{C}}-NH_2,$$

n is three or four and n$^1$ is zero or one; and
corresponding optical isomers thereof or a pharmaceutically acceptable salt thereof.

As neurotensin agonists, the compounds of Formula I are useful as antipsychotic agents for treating psychoses such as schizophrenia. They are also useful as analgesic agents.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

The following table provides a list of abbreviations and definitions thereof used in the present invention.

| Abbreviation* | Amino Acid |
|---|---|
| Arg | Arginine |
| Leu | Leucine |
| Lys | Lysine |
| Pro | Proline |
| Trp | Tryptophan |
| Val | Valine |
| Abbreviation* | Modified and Unusual Amino Acid and Peptides |
| Tle | 3-Methyl valine |
| BAP | Bis(3-aminopropyl)acetyl |
| BAB | Bis(4-aminobutyl)acetyl |
| BGP | Bis(3-guanidinylpropyl)acetyl |
| Arg[ΨCH$_2$NH]Lys | Arg$^1$—Lys |
| Lys[ΨCH$_2$NH]Arg | Lys$^1$—Arg |
| Arg[ΨCH$_2$NH]Arg | Arg$^1$—Arg |
| Lys[ΨCH$_2$NH]Lys | Lys$^1$—Lys |
| Arg[ΨCH$_2$CH$_2$]Arg | Arg$^2$—Arg |
| Lys[ΨCH$_2$CH$_2$]Lys | Lys$^2$—Lys |
| Arg[ΨCH$_2$CH$_2$]Lys | Arg$^2$—Lys |
| Lys[ΨCH$_2$CH$_2$]Arg | Lys$^2$—Arg |
| Abbreviation | Protecting Group |
| Z | Benzyloxycarbonyl |
| BOC | tertiary Butyloxycarbonyl |
| Tos | 4-Toluenesulfonyl (tosyl) |
| MTR | 4-Methoxy-1,2,6-trimethyl-phenylsulfonyl |
| OEt | O-Ethyl |
| OPNP | O-para-nitrophenyl |
| PTH | Pthalimido |
| Abbreviation | Solvents and Reagents |
| HOAc | Acetic acid |
| DMF | Dimethylformamide |
| HCl | Hydrochloric acid |
| KOH | Potassium hydroxide |
| TFA | Trifluoroacetic acid |
| MeOH | Methanol |
| MgSO$_4$ | Magnesium sulfate |
| CHCl$_3$ | Chloroform |
| EtOAc | Ethyl acetate |
| Na$_2$SO$_4$ | Sodium sulfate |
| NaOH | Sodium hydroxide |
| NaHSO$_4$ | Sodium bisulfate |
| KHSO$_4$ | Potassium bisulfate |
| NNM | 1(N)-methyl morpholine |
| ZOSu | Benzyl-succinimidylcarbonate |
| TBTU | 2-(1H-Benzotriazol-1-yl)-1,1,3,3-tetramethyluronium tetrafluoroborate |
| NH$_3$ | Ammonia |
| THF | Tetrahydrofuran |
| LAH | Lithium aluminum hydride |
| NaCNBH$_3$ | Sodium cyanoborohydride |
| PTSA | para-Toluenesulfonic acid |
| NaH | Sodium hydride |
| CH$_2$N$_2$ | Diazomethane |
| PPh$_3$ | Triphenylphosphine |
| CBr$_4$ | Carbon tetrabromide |
| H$_2$ | Hydrogen |

*If the optical activity of the amino acid is other than L(S), the amino acid or abbreviation is preceded by the appropriate configuration D(R) or DL(RS).
$^1$dipeptide amide carbonyl replaced with CH$_2$
$^2$dipeptide amide bond replaced with —CH$_2$CH$_2$—

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge SM, et al, "Pharmaceutical Salts," *Journal of Pharmaceutical Science*, 1977;66:1–19).

The acid addition salts of said basic compounds are prepared by contacting the free base form with a sufficient amount of the desired acid to produce the salt in the conventional manner. Preferably a peptide of Formula I can be converted to an acidic salt by treating with an aqueous solution of the desired base, such that the resulting pH is less than four. The solution can be passed through a C-18 cartridge to absorb the peptide, washed with copious amounts of water, the peptide eluted with a polar organic solvent such as, for example, methanol, acetonitrile, and the like, and isolated by concentrating under reduced pressure followed by lyophilization. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al, "Pharmaceutical Salts," *Journal of Pharmaceutical Science*, 1977;66;1–19).

The base addition salts of said acidic compounds are prepared by contacting the free acid form with a sufficient amount of the desired base to produce the salt in the conventional manner. Preferably, a peptide of Formula I can be converted to a base salt by treating with an aqueous solution of the desired base, such that the resulting pH is greater than nine. The solution can be passed through a C-18 cartridge to absorb the peptide, washed with copious amounts of water, the peptide eluted with a polar organic solvent such as, for example, methanol, acetonitrile and the like, and isolated by concentrating under reduced pressure followed by lyophilization. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forths and are intended to be encompassed within the scope of the present invention.

Certain of the compounds of the present invention possess one or more chiral centers and each center may exist in the R(D) or S (L) configuration. The present invention includes all enantiomeric and epimeric forms as well as the appropriate mixtures thereof.

A preferred embodiment is a compound of Formula I wherein X is NH.

Particularly valuable are:

Arg [ΨCH$_2$NH]Lys-Pro-Trp-Tle-Leu-OEt (Seq ID No: 4);

Arg [ΨCH$_2$NH]Lys-Pro-Trp-Tle-Leu ( Seq ID No: 4);

Lys [ΨCH$_2$NH]Lys-Pro-Trp-Tle-Leu-OEt (Seq ID No: 5);

Lys [ΨCH$_2$NH]Lys-Pro-Trp-Tle-Leu (Seq ID No: 5);

H$_2$N (CH$_2$)$_6$[ΨCH$_2$NH]Lys-Pro-Trp-Tle-Leu-OEt (Seq ID No: 6);

H2N (CH$_2$) 6 [ΨCH$_2$NH]Lys-Pro-Trp-Tle-Leu (Seq ID No: 6);

BAP-Pro-Trp-Tle-Leu-OEt (Seq ID No: 7);
BAP-Pro-Trp-Tle-Leu (Seg ID No: 7);
BAB-Pro-Trp-Tle-Leu-OEt (Seq ID No: 7);
BAB-Pro-Trp-Tle-Leu (Seq ID No: 7);
BGP-Pro-Trp-Tle-Leu-OEt (Seq ID No: 7); and
BGP-Pro-Trp-Tle-Leu (Seg ID No: 7);

or a pharmaceutically acceptable acid addition salt thereof.

The compounds of Formula I are valuable neurotensin agonists. The tests employed indicate that compounds of Formula I possess antipsychotic activity as well as analgesic activity.

Thus, the compounds of Formula I were tested for their ability to inhibit [$^3$H] neurotensin binding in a receptor assay described by Mazella J, et al, *Journal of Biological Chemistry* 1988;263:144–149 and Kitabgi P, et al, *European Journal of Pharmacology* 1987;140: 285–93. Compounds of Formula I were also tested for their ability to inhibit locomotor activity in mice according to the assay described by McLean JR, et al, *Pharmacology, Biochemistry and Behavior* 1978;8:97-99.

Compounds of Formula I were also tested for their ability to inhibit acetic acid-induced writhing in the mouse according to the method described by Koster R, et al, *Federation Proceedings* 1959;1626:412 and for their antinociceptive activity in the rat tail pressure test according to the modification outlined in Winder CV, et al, *Arch Int Pharmacodyn Ther* 1959;122: 301-11 of the method of Green AF, *Br J Pharmacol* 1951;6:572-87. The above test methods are incorporated herein by reference. The data in the table show the neurotensin receptor binding activity, antipsychotic activity, and analgesic activity of representative compounds of Formula I.

| | Biological Activity of Compounds of Formula I | | | | |
|---|---|---|---|---|---|
| Example Number | Compound | Inhibition of [$^3$H] Neurotensin Binding Ki, nM | Inhibition of Locomotor Activity in Mice ED$_{50}$, mg/kg, IP | Inhibition of Acetic Acid-Induced Writhing in Mice ED$_{50}$, mg/kg, IP | Rat Tail Pressure Protocol in Rats ED$_{50}$, mg/kg |
| 1 | Arg[ΨCH$_2$NH]Lys—Pro—Trp—Tle—Leu—OEt (Seq ID No: 4) | 437 | 0.17 | 0.1 | 0.3 |
| 2 | Arg[ΨCH$_2$NH]Lys—Pro—Trp—Tle—Leu (Seq ID No: 4) | 17.1 | 0.48 | 0.1 | |
| 3 | Lys[ΨCH$_2$NH]Lys—Pro—Trp—Tle—Leu—OEt (Seq ID No: 5) | 31.2 | 0.2 | 0.06 | |
| 4 | Lys[ΨCH$_2$NH]Lys—Pro—Trp—Tle—Leu (Seq ID No: 5) | 1.3 | 0.14 | 0.06 | |
| 5 | H$_2$N(CH$_2$)$_6$[ΨCH$_2$NH]—Lys—Pro—Trp—Tle—Leu—OEt (Seq ID No: 6) | 27 | 0.3 | | |
| 8 | BAP—Pro—Trp—Tle—Leu (Seq ID No: 7) | 14 | 0.5 | | |
| 10 | BAB—Pro—Trp—Tle—Leu (Seq ID No: 7) | 1 | 0.6 | | |
| 12 | BGP—Pro—Trp—Tle—Leu (Seq ID No: 7) | 0.10 | | | |
| * | Lys[ΨCH$_2$NH]Lys—Pro—Tyr—Ile—Leu (Seq ID No: 2) | 0.15 | NA † | 1.0 | NA** |

*Lugrin D, et al, European Journal of Pharmacology 1991; 205:191-8
**Not active at 3 mg/kg
† Not active at 10 mg/kg Also, the present invention provides a process for the preparation of compounds of Formula I Thus, a compound of Formula Ia

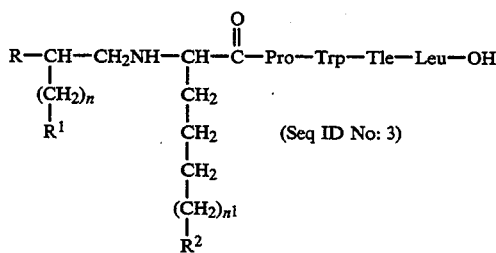

(Seq ID No: 3)

wherein

R is H or NH$_2$;

R$^1$ and R$^2$ are each independently NH$_2$ or

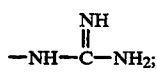

n is zero or an integer of one to four;

n$^1$ is zero or one; provided:

when R is H then R$^1$ is NH$_2$, R$^2$ is NH$_2$ or

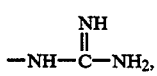

n is zero or an integer of one to four and n$^1$ is zero or one;

when R is NH$_2$ then R$^1$ and R$^2$ are NH$_2$ or

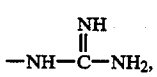

n is three or four, and n$^1$ is zero or one;

and corresponding optical isomers thereof or a pharmaceutically acceptable salt thereof may be prepared by hydrolyzing a compound of Formula Ib

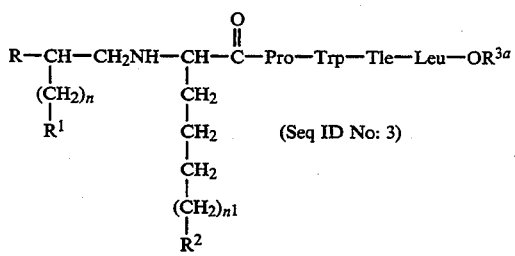

wherein R$^{3a}$ is lower alkyl and R, R$^1$, R$^2$, n, and n$^1$ are as defined above with a base such as, for example, an alkali metal hydroxide, for example sodium hydroxide, potassium hydroxide and the like in water to afford a compound of Formula Ia. Preferably, the reaction is carried out with sodium hydroxide in water.

A compound of Formula Ib-1 is prepared by treatment of a compound of Formula II

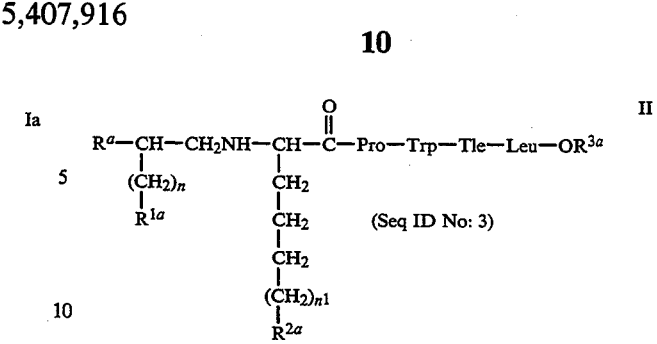

wherein

R$^a$ is BOC-NH or Z—NH—;

R$^{1a}$ and R$^{2a}$ are each independently BOC—NH— or

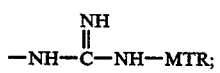

and R$^{3a}$, n, and n$^1$ are as defined above with an acid such as, for example, trifluoroacetic acid and the like in the presence of anisole, thioanisole, and ethane dithiol and the like to afford a compound of Formula Ib-1. In the case wherein R$^a$ is —Z—NH—, the benzyloxycarbonyl (Z) group is removed by treatment with hydrogen and a catalyst such as, for example, 20% palladium on carbon and a solvent such as, for example, ethanol and the like prior to treatment with an acid as described above. Preferably, the reaction is carried out with either trifluoroacetic alone or pretreatment with hydrogen and 20% palladium on carbon in ethanol followed by treatment with trifluoroacetic acid.

A compound of Formula IIa wherein R$^a$ is —Z—NH—;

R$^{1a}$ is BOC—NH—; R$^{2a}$ is BOC—NH—or

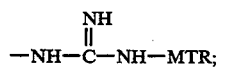

and R$^{3a}$, n, and n$^1$ are as defined above is prepared by reacting a compound of Formula III

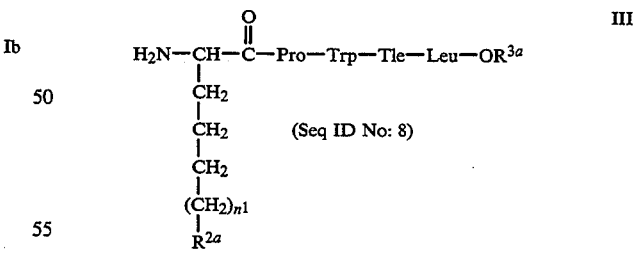

wherein R$^{2a}$, R$^{3a}$, and n$^1$ are as defined above with a compound of Formula IVa

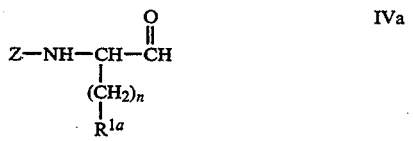

wherein R$^{1a}$ and n are as defined above with a metal hydride such as, for example, sodium cyanoborohydride and the like in a solvent such as, for example, methanol and the like containing an acid such as, for example, acetic acid to afford a compound of Formula IIa. Preferably, the reaction is carried out with sodium cyanoborohydride in methanol containing about 1% to about 10% acetic acid.

A compound of Formula IVa is prepared from the corresponding carboxylic acid by conversion to the $N(CH_3)OCH_3$ amide and reduction with LAH using conventional methodology known in the art.

A compound of Formula IIb wherein $R^a$ is BOC—NH—; $R^{1a}$ is

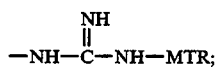

$2^{2a}$ is BOX—NH— or

n is an integer of three; and $R^{3a}$ and $n^1$ are as defined above is prepared by reacting a compound of Formula III with a compound of Formula V (Seg ID No: 7)

wherein $R^{3a}$ is as defined above with a compound of Formula VIII

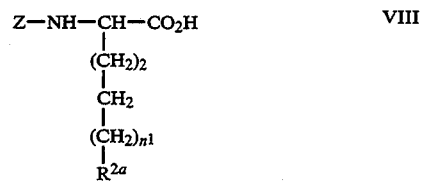

wherein $R^{2a}$, $n^1$, and Z are as defined above in the presence of a coupling reagent such as, for example, 2-(1Hbenzotriazol-l-yl)-1,1,3,3,-tetramethyluronium fluroborate) (TBTU) and the like in the presence of 1(N)-methyl morpholine (NMN) in a solvent such as, for example, dimethylformamide and the like followed by removal of the benzyloxycarbonyl protecting group with hydrogen in the presence of a catalyst such as, for example, palladium on charcoal and the like to afford a compound of Formula III. Preferably, the reaction is carried out with TBTU in the presence of NMN in DMF followed by hydrogenation in the presence of palladium on carbon.

SCHEME I

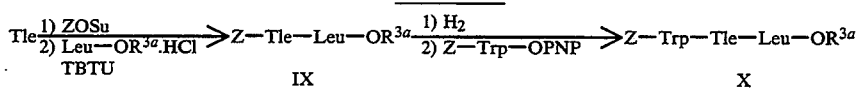

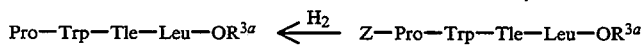

VII
(Seq ID No: 7)

XI
(Seq ID No: 7)

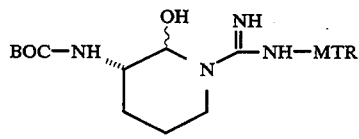

using the methodology described above for preparing a compound of Formula IIa from a compound of Formula III and a compound of Formula IVa.

A compound of Formula V is prepared from the compound of Formula VI

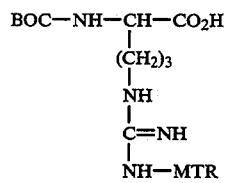

by reaction with carbonyl diimidazole in tetrahydrofuran and subsequent reaction with lithium aluminum hydride to afford the compound of Formula V.

A compound of Formula III is prepared by reacting a compound of Formula VII

     

A compound of Formula VII is prepared as described in Scheme I. Thus, a compound of Formula IX wherein $R^{3a}$ and Z are as defined above is prepared by reacting Tle with benzylsuccimidylcarbonate (ZOSu) in the presence of a base such as, for example, sodium carbonate and the like in a solvent such as, for example, tetrahydrofuran and the like followed by subsequent coupling of Z-Tle with a compound of Formula Leu-OR$^{3a}$·HCl wherein $R^{3a}$ is as defined above in the presence of TBTU and NMN in dimethylformamide to afford the compound of Formula IX. Preferably, the reaction is carried out with Z-OSu and sodium carbonate in tetrahydrofuran and subsequent reaction of Z-Tle with Leu-OR$^{3a}$ in the presence of TBTU and NMN in dimethylformamide.

A compound of Formula X wherein $R^{3a}$ and Z are as defined above is prepared by reacting a compound of Formula IX with hydrogen in the presence of a catalyst such as, for example, palladium on carbon and subsequent coupling of Tle-Leu-OR$^{3a}$ with Z-Trp-OPNP in the presence of NMM in dimethylformamide to afford a compound of Formula X. Preferably, the reaction is carried out with hydrogen in the presence of palladium on carbon and subsequent reaction of Tle-Leu-OR$^{3a}$ with Z-Trp-OPNP in the presence of NMM in dimethylformamide.

A compound of Formula XI wherein R$^{3a}$ and Z are as defined above is prepared by reacting a compound of Formula X with hydrogen in the presence of a catalyst such as, for example, palladium on carbon and subsequent coupling of Trp-Tle-Leu-OR$^{3a}$ with Z-Pro in the presence of TBTU in the presence of NMM in dimethylformamide to afford a compound of Formula XI. Preferably, the reaction is carried out with hydrogen in the presence of palladium on carbon and subsequent reaction of Trp-Tle-Leu-OR$^{3a}$ with Z-Pro in the presence of TBTU and NMN in dimethylformamide.

A compound of Formula VII wherein R$^{3a}$ is as defined above is prepared by reacting a compound of Formula XI with hydrogen in the presence of a catalyst such as, for example, palladium on carbon to afford a compound of Formula VII. Preferably, the reaction is carried out with hydrogen in the presence of palladium on carbon.

A compound of Formula Ia-1 wherein R is H; X is NH; R$^1$ is NH$_2$; is NH$_2$ or

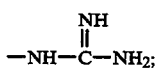

n is zero or an integer of one to four; and n$^1$ is zero or one may be prepared from a compound of Formula Ib-1 by hydrolysis with a base such as, for example, sodium hydroxide and the like as outlined in Scheme II. A compound of Formula Ib-1 is prepared from a compound of Formula XII by hydrolysis with an acid such as, for example, trifluoroacetic acid and the like to afford a compound of Formula Ib-1. A compound of Formula XII is prepared by reacting a compound of Formula III with a compound of Formula IVb in the presence of a metal hydride such as, for example, sodium cyanoborohydride and the like and a dilute organic acid such as, for example, acetic acid and the like to afford a compound of Formula XII. A compound of Formula IVb is prepared from a carboxylic acid of Formula XIII using conventional methodology.

SCHEME II

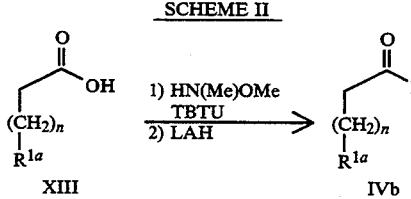

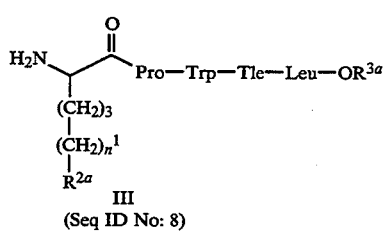
III
(Seq ID No: 8)

-continued
SCHEME II

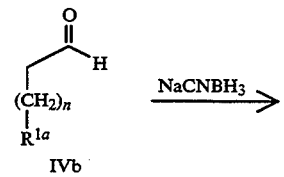
IVb

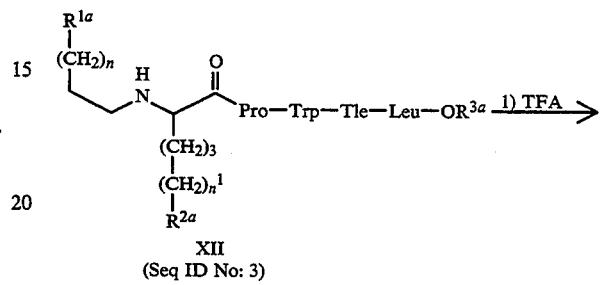
XII
(Seq ID No: 3)

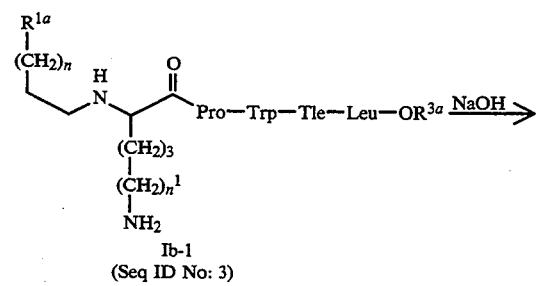
Ib-1
(Seq ID No: 3)

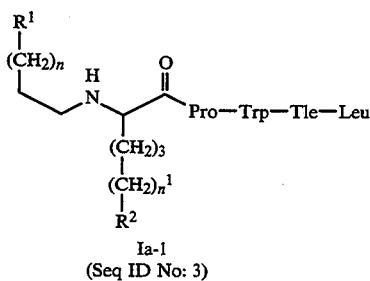
Ia-1
(Seq ID No: 3)

In the above structures, n is zero or an integer of one to four and n$^1$ is zero or one, R$^{1a}$ is —NH—BOC, R$^{2a}$ is —NHBOC or

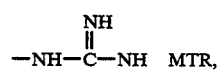

R$^1$ is NH$^2$, R$^2$ is NH$_2$ or

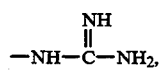

and R$^{3a}$ is lower alkyl.

A compound of Formula Ic $$R-CH-CH_2-CH_2-CH-\overset{O}{\overset{\|}{C}}-Pro-Trp-Tle-Leu-OH \quad \text{Ic}$$
$$\underset{R^1}{\overset{(CH_2)_n}{|}} \quad \underset{\underset{R^2}{(CH_2)_{n1}}}{\overset{CH_2}{\underset{|}{\overset{|}{CH_2}}}}$$

(Seq ID No: 3)

wherein
R is H or $NH_2$;
$R^1$ and $R^2$ are each independently $NH_2$ or $$-NH-\overset{NH}{\overset{\|}{C}}-NH_2;$$

n is zero or an integer of one to four;
$n^1$ is zero or one; provided:
when R is H then $R^1$ and $R^2$ are $NH_2$;
$n^1$ is zero or an integer of one to four and $n^1$ is zero or one;
when R is $NH_2$ then $R^1$ is $NH_2$ or $$-NH-\overset{NH}{\overset{\|}{C}}-NH_2,$$

$R^2$ is $NH_2$, n is three or four, and $n^1$ is zero or one is prepared from a compound of Formula Id using methodology used to prepare a compound of Formula Ia from a compound of Formula Ib $$R-CH-CH_2-CH_2-CH-\overset{O}{\overset{\|}{C}}-Pro-Trp-Tle-Leu-OR^{3a} \quad \text{Id}$$
$$\underset{R^1}{\overset{(CH_2)_n}{|}} \quad \underset{\underset{R^2}{(CH_2)_{n1}}}{\overset{(CH_2)_3}{|}}$$

(Seq ID No: 3)

A compound of Formula Id wherein
R is $NH_2$; $R^1$ is $NH_2$ or $$NH-\overset{NH}{\overset{\|}{C}}-NH_2;$$

$R^2$ is $NH_2$;
n is three or four; and $n^1$ is zero or one and $R^{3a}$ is lower alkyl is prepared from a compound of Formula XIV $$R^a-CH-CH_2-CH_2-CH-\overset{O}{\overset{\|}{C}}-Pro-Trp-Tle-Leu-OR^3 \quad \text{XIV}$$
$$\underset{R^{1a}}{\overset{(CH_2)_n}{|}} \quad \underset{\underset{R^{2a}}{(CH_2)_{n1}}}{\overset{(CH_2)_3}{|}}$$

(Seq ID No: 3)

wherein
$R^a$ is BOC—NH—;
$R^{1a}$ is BOC—NH or $$-NH-\overset{NH}{\overset{\|}{C}}-NH-MTR;$$

and $R^{2a}$ is PTNH;
When $R^a$ is H, $R^{1a}$ and $R^{2a}$ are PTNH;
and n, $n^1$, and $R^{3a}$ are as defined above by removal of the amino protecting groups by conventional methodology such as used for the conversion of a compound of Formula II to a compound of Formula Ib-1. The PTH group is removed with hydrazine.

When $R^a$ is BOC-NH a compound of Formula XIV may be prepared as outlined in Scheme III.

Thus, a compound of Formula XIV is prepared by reaction of a compound of Formula XV with a compound of Formula VII in the presence of TBTU. A compound of Formula XV can be prepared by reacting a compound of Formula XVI with a compound of Formula XVII in the presence of a strong base such as, for example, sodium hydride and the like. A compound of Formula XVI may be prepared using conventional methodology known in the art, e.g., reduction of an ester of Formula XVIII and subsequent bromination of the resulting alcohol to afford a compound of Formula XVI. An ester of Formula XVIII may be obtained via Wolff rearrangement of a diazoketone of Formula XIX as reported by Kline, et al, *Biochem and Biophys Res Comm* 1991;177:1049-55. A compound of Formula XIX may be prepared by reaction of an acid chloride of Formula XX with diazomethane. An acid chloride of Formula XX may be prepared by conventional methodology known in the art. A compound of Formula XVII may be prepared from di-tertiary butyl malonate and one equivalent of a compound of Formula XXI.

SCHEME III $$R^{2a}(CH_2)_{n1}-Br \quad tBuO_2C\diagdown CO_2tBu \xrightarrow{1)\ NaH}$$
XXI $$\begin{array}{c} tBuO_2C\diagdown CO_2tBu \\ | \\ (CH_2)_3 \\ | \\ (CH_2)_{n1} \\ | \\ R^{2a} \end{array}$$
XVII $$BOCHN\diagdown \overset{O}{\overset{\|}{C}}-Cl \xrightarrow{CH_2N_2}$$
$$\underset{R^{1a}}{\overset{(CH_2)_n}{|}}$$
XX $$BOCHN\diagdown \overset{O}{\overset{\|}{C}}-CHN_2 \xrightarrow{heat}$$
$$\underset{R^{1a}}{\overset{(CH_2)_n}{|}}$$
XIX -continued
SCHEME III

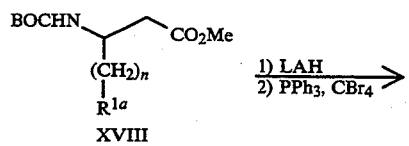

XVIII

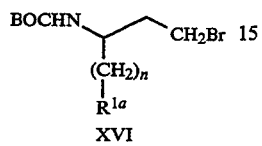

XVI

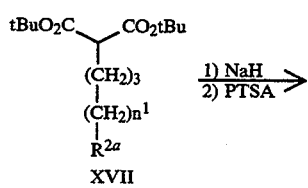

XVII

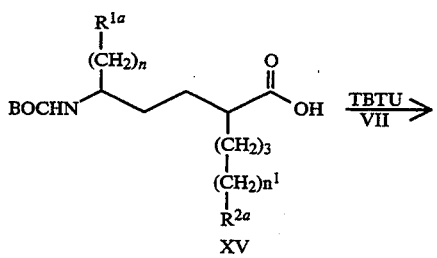

XV

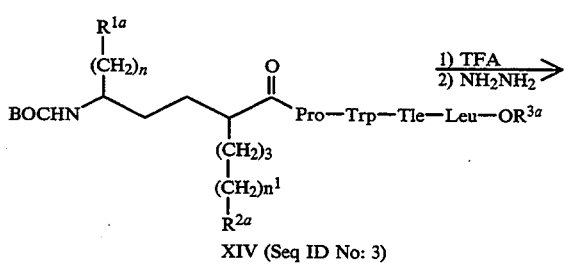

XIV (Seq ID No: 3)

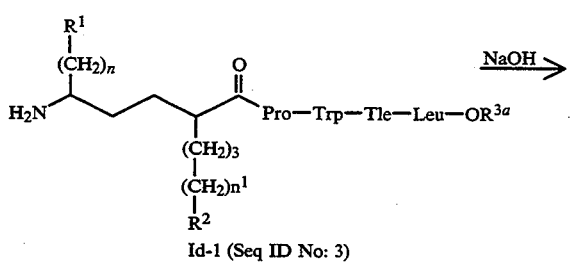

Id-1 (Seq ID No: 3)

-continued
SCHEME III

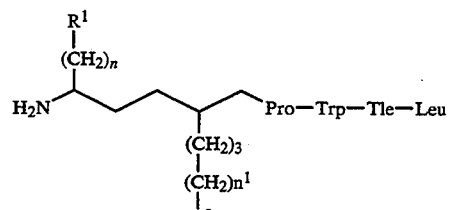

Ic-1 (Seq ID No: 3)

In the above structures, $R^1$ is $NH_2$ or

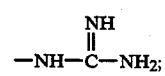

$R^2$ is $NH_2$; $R^{1a}$ is BOCHN or

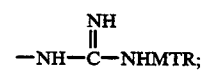

$R^{2a}$ is —NPTH; $R^{3a}$ is lower alkyl; n is three or four; and $n^1$ is zero or one.

A compound of Formula Id-2 wherein R is H, $R^1$ and $R^2$ are $NH_2$, n is zero or an integer of one to four, and $n^1$ is zero or one is prepared as outlined in Scheme IV from a compound of Formula XXII wherein $R^{1a}$ and $R^{2a}$ are PTHN, $R^{3a}$, n, and $n^1$ as described above.

A compound of Formula XXII may be prepared from a compound of Formula XXIII and a compound of Formula VII in the presence of a coupling reagent such as, for example, TBTU and the like. A compound of Formula XXIII may be prepared from a compound of Formula XVII and a compound of Formula XXXIV in the presence of a strong base such as, for example, sodium hydroxide and the like and subsequent decarboxylation of the resulting intermediate with an acid such as, for example, para-toluenesulfonic acid and the like to afford a compound of Formula XXIII.

A compound of Formula Ic-2 wherein $R^1$ and $R^2$ are $NH_2$, and n and $n^1$ are both zero or one is prepared as outlined in Scheme V from a compound of Formula Id-2 wherein $R^{3a}$ is lower alkyl and $R^1$, $R^2$, n, and $n^1$ are as defined above by hydrolysis catalysed by a base such as, for example, sodium hydroxide in a solvent such as, for example, ethanol.

A compound of Formula Id-2 can be prepared from a compound of Formula XXVIII wherein $R^{1b}$ and $R^{2b}$ are Z—NH— and n, $n^1$, and $R^{3a}$ are as defined above by reacting a compound of Formula XXVIII with hydrogen in the presence of a catalyst such as, for example, palladium on carbon, in a solvent such as, for example, ethanol.

A compound of Formula XXVIII can be prepared from a compound of Formula XXVII wherein $R^{1b}$, $R^{2b}$, n, and $n^1$ are as defined above by reacting with a strong acid such as, for example, TFA and subsequent coupling with Trp-Tle-Leu-OR$^{3a}$ wherein $R^{3a}$ is as defined above in the presence of TBTU and NMM in DMF.

SCHEME IV
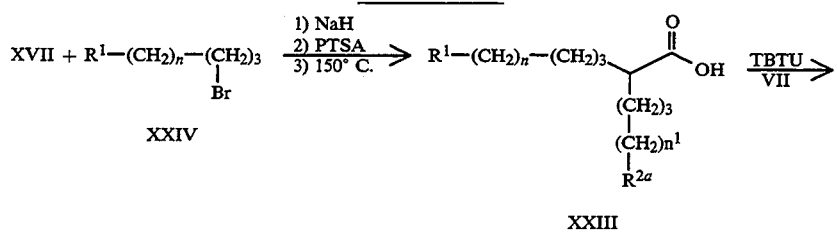
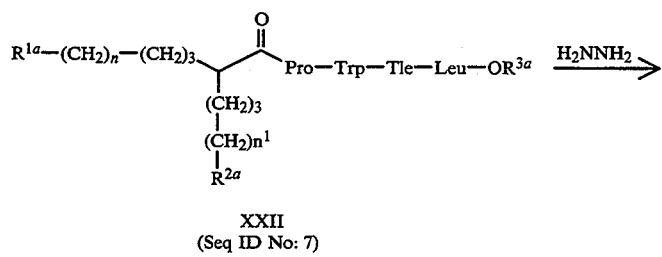
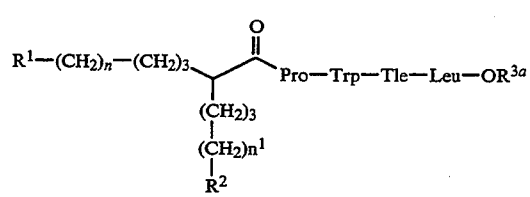
In the above structures, $R^1$ and $R^2$ are $NH_2$, $R^{1a}$ and $R^{2a}$ are PTHN-, $R^{3a}$ is lower alkyl, $n^1$ is zero or one, and n is zero or an integer of one to four.
SCHEME V
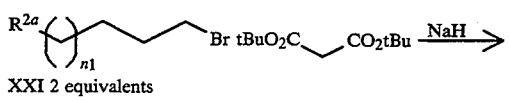
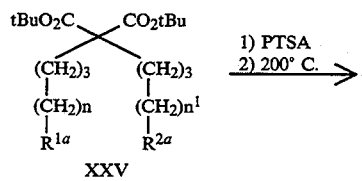
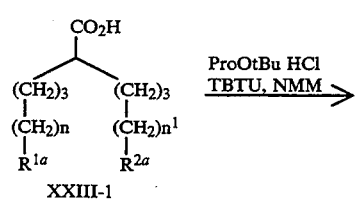
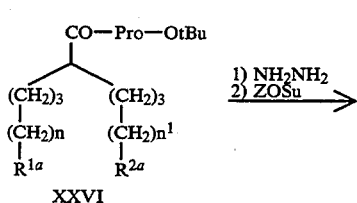
-continued
SCHEME V
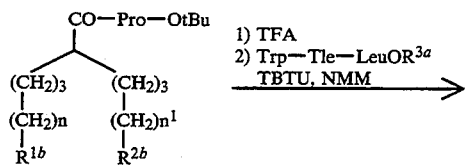
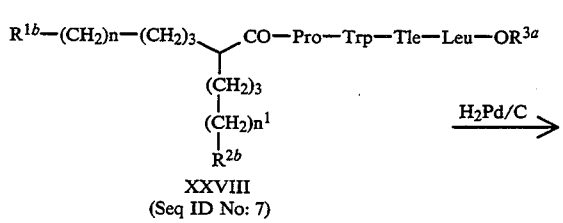
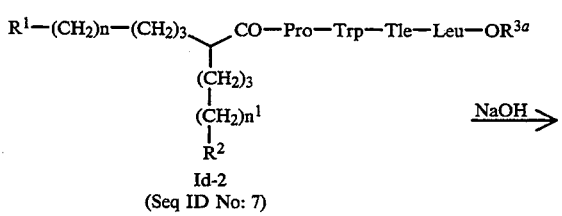
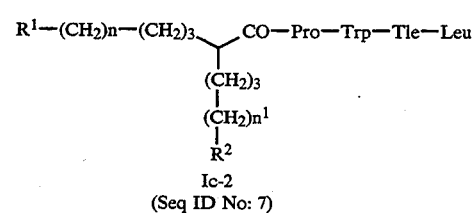

In the above structures, $R^1$ and $R^2$ are $NH_2$, $R^{1a}$ and $R^{2a}$ are PTH-N-, $R^{1b}$ and $R^{2b}$ are —Z—NH—, $R^{3a}$ is lower alkyl, n and $n^1$ are either both zero or one.

A compound of Formula XXVII can be prepared from a compound of Formula XXVI wherein $R^{1a}$ and $R^{2a}$ are PTH-N- and n and $n^1$ are as defined above by reaction with hydrazine and then ZOSu in the presence of a base such as, for example, sodium carbonate.

A compound of Formula XXVI can be prepared by reaction of a compound of Formula XXIII-1 wherein $R^{1a}$, $R^{2a}$, n, and $n^1$ are as defined above by coupling with proline tert-butyl ester hydrochloride in the presence of a coupling agent such as, for example, TBTU in the presence of NMM in a solvent such as, for example, DMF.

A compound of Formula XXIII-1 can be prepared from a compound of Formula XXV wherein $R^{1a}$, $R^{2a}$, n, and $n^1$ are as defined above by treating with PTSA in a refluxing solvent such as, for example, toluene and then heating the resulting product to 200° C to effect decarboxylation.

A compound of Formula XXV can be prepared via reaction of ditertiary butyl malonate with two equivalents of a compound of Formula XXI wherein $n^1$ is zero or one, and $R^{2a}$ is PTH—N— in the presence of two equivalents of a strong base such as, for example, sodium hydride.

A compound of Formula Ic-3 wherein $R^1$ and $R^2$ are

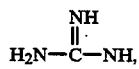

n and $n^1$ are both zero or one is prepared as outlined in Scheme VI from a compound of Formula Id-3 wherein $R^{3a}$ is lower alkyl and $R^1$, $R^2$, n, and $n^1$ are as defined above by hydrolysis catalysed by a base such as, for example, sodium hydroxide in a solvent such as, for example, ethanol.

A compound of Formula Id-3 can be prepared from a compound of Formula XXX, wherein $R^{1c}$ and $R^{2c}$ are

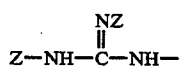

and n $n^1$ and $R^{3a}$ are as defined above by reacting with hydrogen in the presence of a catalyst such as, for example, palladium on carbon in a solvent such as, for example, ethanol.

A compound of Formula XXX can be prepared from a compound of Formula XXIX wherein Rlc, $R^{2c}$, n, and $n^1$ are as defined above by reacting with a strong acid such as, for example, TFA and subsequent coupling with Trp-Tle-Leu-$OR^{3a}$ wherein $R^{3a}$ is as defined above in the presence of TBTU and NMM in DMF.

A compound of Formula XXIX can be prepared from a compound XXVII, wherein $R^{1b}$ and $R^{2b}$ are —Z—NH—and n and $n^1$ are as defined above by reacting with hydrogen in the presence of a catalyst such as, for example, palladium on carbon and then with N,N-bis (benzyloxycarbonyl)-S-methyl thiourea in the presence of a base such as, for example, DMF.

Compounds of Formula IVa, Formula VI, Formula VIII, Formula XIII, Formula XXI, and Formula XXIV are either known or capable of being prepared by methods known in the art.

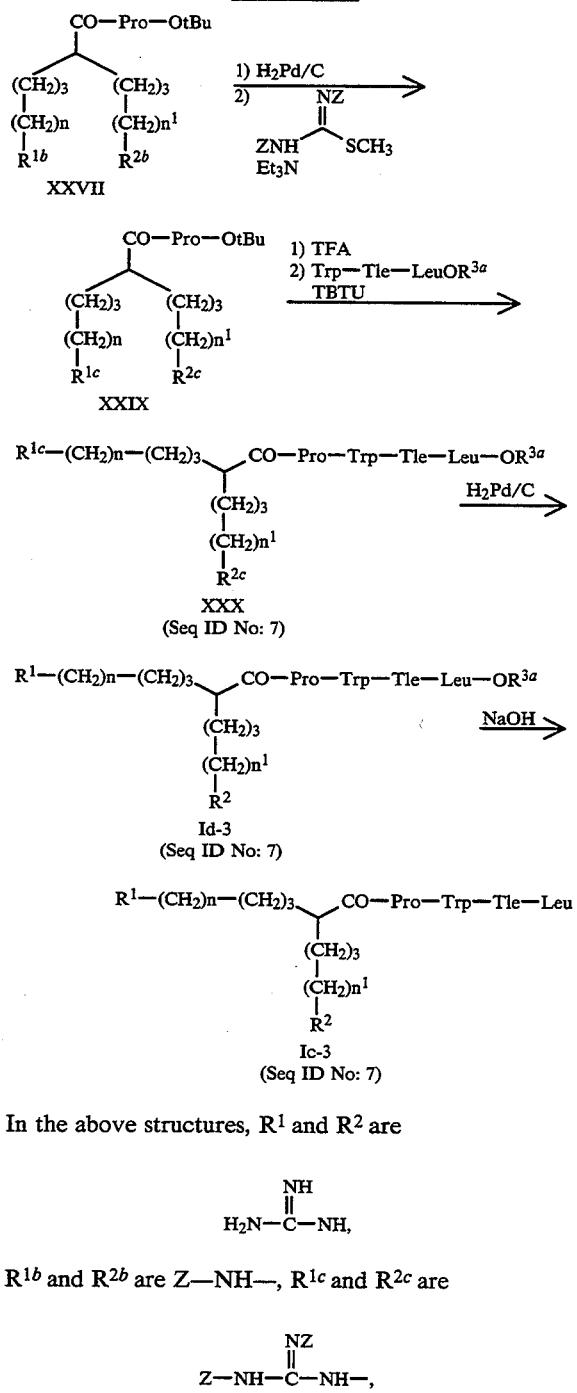

In the above structures, $R^1$ and $R^2$ are

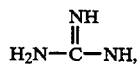

$R^{1b}$ and $R^{2b}$ are Z—NH—, $R^{1c}$ and $R^{2c}$ are

$R^{3a}$ is lower alkyl, n and $n^1$ are either both zero or one.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antipsychotic or analgesic agents, the compounds utilized in the pharmaceutical method of this invention are administered at the initial dosage of about 0.01 mg to about 50 mg per kilogram daily. A daily dose range of about 0.01 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the inventors preferred methods for preparing the compounds of the invention.

EXAMPLE 1

Arg[$\Psi$CH$_2$NH]Lys-Pro-Trp-Tle-Leu-OEt-TFA(1:3) (L-Leucine, N-[N-[N-[1-[N$^2$-[2-amino-5-[aminoimimomethyl)amino]-pentyl -L-lysyl]-L-prolyl-L-tryptophyl]-3-methyl-L-valyl]-, ethyl ester, (S)-, trifluoroacetate (1:3) (salt)) (Seq ID No: 4)

Step A: Preparation of Z-Tle

L-Tle (7.76 g, 59.1 mmol) is dissolved in 235 mL of 6% sodium carbonate and treated with ZOSu (16.2 g, 65.01 mmol) in 60 mL THF. The resulting mixture is stirred at room temperature for 3 hours. The THF is removed under reduced pressure and the mixture is extracted with 250 mL portions of diethyl ether (2×) which are discarded. The aqueous fraction is carefully acidified with 1 M HCl to pH 4.5 and then is extracted with 250 mL portions of diethyl ether (2×). The ethereal extracts are treated with brine and dried over MgSO$_4$ and then evaporated under reduced pressure to obtain Z-Tle (15.6 g). Fast Atom Bombardment Mass Spectrometry (FABMS) M+1 266

Step B: Preparation of Z-Tle-Leu-OEt

Z-Tle (15.6 g, 59.1 mmol), Leu-OEt HCl (11.56 g, 59.1 mmol), and N-methyl morpholine (NMM) (12.75 mL) are mixed with 45 mL of DMF and a cloudy suspension forms. The mixture is cooled to 0° C. and treated with TBTU (19.1 g, 59.48 mmol), then stirred at 0° C. for 15 minutes, then removed from the cold bath and stirred for 1.5 hours. The mixture is poured into 500 mL of a saturated solution of sodium carbonate which is then extracted with two 350 mL portions of ethyl acetate. The combined organic extracts are washed with 500 mL of 1 M KHSO$_4$ water and brine and then dried over sodium sulfate. The solvents are removed to give Z-Tle-Leu-OEt (24.1 g). FABMS M+1 407

Step C: Preparation of Z-Trp-Tle-Leu-OEt

A solution of Tle-Leu-OEt (3.41 g, 12.5 mmol) (prepared by catalytic hydrogenation of Z-Tle-Leu-OEt over palladium on charcoal), Z-tryptophan p-nitrophenol ester (5.77 g, 12.55 mmol), and NMM (0.5 mL) in 20 mL DMF is stirred at room temperature for 18 hours. The reaction is poured into 200 mL of a saturated solution of sodium bicarbonate and extracted with 350 mL of ethyl acetate. The organic extract is washed with 1 M KHSO$_4$, water, brine, and dried over Na$_2$SO$_4$. The solvents are removed under reduced pressure to give Z-Trp-Tle-Leu-OEt (6.3 g). FABMS M+1 593

Step D: Preparation of Z-Pro-Trp-Tle-Leu-OEt (Seq ID No: 7)

Z-Pro (2.18 g, 8.3 mmol) and Trp-Tle-Leu-OEt (prepared by catalytic hydrogenation of Z-Trp-Tle-Leu-OEt over palladium on charcoal) (3.47 g, 7.6 mmol), and NMM (0.92 mL) are dissolved in 35 mL DMF, cooled to 0° C., and treated with TBTU (2.66 g, 8.3 mmol). The reaction is stirred at 0° C. for 1 hour then removed from the ice bath and stirred at room temperature for 2 hours. The mixture is poured into 350 mL of a saturated solution of sodium bicarbonate which is then extracted with 350 mL of ethyl acetate. The combined organic extracts are washed with 350 mL of 1 M KHSO$_4$, water and brine, and then dried over sodium sulfate. The solvents are removed and the residue chromatographed on silica gel (1.5% MeOH in chloroform) to give Z-Pro-Trp-Tle-Leu-OEt (Seq ID No: 7) (4.7 g). FABMS M+1 690

Step E: Preparation of Z-Lys(BOC)-Pro-Lys-Tle-Leu-OEt (Seq ID No: 9)

Z-Lys(BOC) (0.75 g, 1.98 mmol), Pro-Trp-Tle-Leu-OEt (Seq ID No: 7), (1.0 g, 1.8 mmol) (prepared by catalytic hydrogenation of Z-Pro-Tle-Leu-OEt (Seq ID No: 7) over palladium on charcoal), and NMM (0.36 mL) is dissolved in 15 mL DMF, cooled to 0° C., and treated with TBTU (0.635 g, 1.98 mmol). The reaction is stirred at 0° C. for 1 hour then removed from the ice bath and stirred at room temperature for 3 hours. The mixture is poured into 150 mL of a saturated solution of sodium carbonate which is then extracted with two 150 mL portions of ethyl acetate. The combined organic extracts are washed with 150 mL of 1 M KHSO$_4$, water and brine, and then dried over sodium sulfate. The solvents are removed under reduced pressure and the residue is chromatographed on silica gel. (2% MeOH in chloroform with 0.1% NH$_3$) to give Z-Lys(BOC)-Pro-Trp-Tle-Leu-OEt (Seq ID No: 9) (1.34 g). FABMS M+1 818 (M-tBu)

Step F: Preparation of BOC-Arg(MTR) Aldehyde

BOC-Arg(MTR) (9.0 g, 18.5 mmol) is dissolved in THF (90 mL) cooled to -10° C. and treated with carbonyl diimidazole (3.3 g, 20.3 mmol). After 20 minutes the reaction is cooled to −50° C. and lithium aluminum hydride (22.2 mL of a 1 M solution THF) is added over 45 minutes. The reaction is then allowed to warm to −10° C. over 1 hour and is treated with a solution of 4.5 g of NaHSO$_4$ in 90 mL of water. The reaction is warmed to room temperature and the THF is removed under reduced pressure. The resulting aqueous mixture is extracted with two 150 mL portions of ethyl acetate. The combined organic extracts are washed with brine, dried over sodium sulfate, and the solvents are removed under reduced pressure. The resulting residue is chromatographed over silica gel (1–2% MeOH in chloroform) to give BOC-Arg(MTR) Aldehyde (4.02 g). FABMS M+1 471

Step G: Preparation of Lys(BOC)-Pro-Trp-Tle-Leu-OEt (Seq ID No: 9)

Z-Lys (BOC) -Pro-Trp-Tle-Leu-OEt (Seq ID No: 9) (Step E) (1.57 g, 1.7 mmol) is dissolved in 100 mL of ethanol, treated with 0.5 g of 20% palladium on carbon and placed under 50 pounds per square inch (psi) of hydrogen. After 18 hours the reaction is filtered and the solvent is removed under reduced pressure to give Lys(BOC)-Pro-Trp-Tle-Leu-OEt (Seq ID No: 9) (1.36 g) . FABMS M+1 784

Step H: Preparation of BOC-Arg(MTR) [ΨCH$_2$NH]Lys(BOC)-Pro-Trp-Tle-Leu-OEt (Seq ID No: 4)

A solution of Lys(BOC)-Pro-Trp-Tle-Leu-OEt (Seq ID No: 9) (1.1 g, 1.4 mmol) and BOC-Arg(MTR) Aldehyde (Step F) (0.72 g, 1.54 mmol) in 15 mL methanol containing 1% acetic acid is treated with three 0.2 g portions of sodium cyanoborohydride over 3 hours. The methanol is removed under reduced pressure and the residue is partitioned between a saturated solution of sodium bicarbonate (30 mL) and chloroform (30 mL), the organic phase is dried over sodium sulfate, evaporated, and the residue chromatographed on silica gel eluted with 2% methanol in chloroform containing 0.1% ammonia to give BOC-Arg(MTR)[ΨCH$_2$NH]-Lys(BOC)-Pro-Trp-Tle-Leu-OEt (Seq ID No: 4) (0.90 g). FABMS M+1 1239

Step I: Preparation of Arg[ΨCH$_2$NH]Lys-Pro-Trp-Tle-Leu-OEt (Seq ID No: 4)

BOC-Arg (MTR) [ΨCH$_2$NH]Lys-(BOC)-Pro-Trp-Tle-Leu-OEt (Seq ID No: 4) (0.89 g, 0.72 mmol) is treated with a solution of 23 mL TFA, 1 mL water, 0.5 mL anisole, 1.2 mL thioanisole, and 0.5 mL ethane dithiol and stirred at room temperature for 6.5 hours. The reaction is poured into 400 mL of diethyl ether and allowed to stand overnight and the resulting precipitate is filtered and dried under vacuum. The resulting crude solid was purified by preparative High Performance Liquid Chromatography (HPLC) (C-18, 20–50% acetonitrile in water with 0.1% TFA) to obtain Arg [ΨCH$_2$NH]-Lys-Pro-Trp-Tle-Leu-OEt (Seq ID No: 4) (0.25 g) . FABMS M+1 826

EXAMPLE 2

Arg [ΨCH$_2$NH]Lys-Pro-Trp-Tle-Leu (L-Leucine, N-[N-[N-[1-[N$^2$-[2-amino-5-[(aminoiminomethyl)amino]pentyl]-L-lysyl]-L-prolyl]-L-tryptophyl]-3-methyl-L-valyl]-, (S)-, trifluoroacetate (1:2) salt)) (Seq ID No: 4)

Crude Arg[ΨCH$_2$NH]Lys-Pro-Trp-Tle-Leu-OEt TFA (Seq ID No: 4) (Example 1) (30 mg, 0.02 mmol) is dissolved in 0.3 mL of water, treated with 0.13 mL of a 2N solution of sodium hydroxide, and stirred at room temperature for 2 hours. The reaction is neutralized with HCl and the water is removed under reduced pressure. The resulting crude solid is purified by preparative HPLC (C-18, 20–50% acetonitrile in water with 0.1% TFA) to obtain Arg[ΨCH$_2$NH]Lys-Pro-Trp-Tle-Leu (Seq ID No: 4) (15 mg). FABMS+1 798

EXAMPLE 3

Lys[ΨCH$_2$NH]Lys-Pro-Trp-Tle-Leu-OEt (L-Leucine, N-[N-[N-[1-[N$^2$-(2,6-diaminohexyl)-L-lysyl]-L-prolyl]-L-tryptophyl]-3-methyl-L-valyl]-, ethyl ester, (S)-) (Seq ID No: 5)

Step A: Preparation of BOC-Lys(Z) [ΨCH$_2$NH]Lys (BOC)-Pro-Trp-Tle-Leu-OEt (Seq ID No: 5)

Lys (BOC)-Pro-Trp-Tle-Leu-OEt (Seq ID No: 9) (Example 1, Step G) (1.0 g, 1.27 mmol) and BOC-Lys(Z) aldehyde (0.55 g, 1.5 mmol) are dissolved in 11 mL of a 10% acetic acid in methanol solution. Sodium cyanoborohydride (0.16 g, 2.54 mmol) is added in two portions over 1 hour. The methanol is removed under reduced pressure and the residue is partitioned between 30 mL of chloroform and 30 mL of bicarbonate. The organic layer is dried over sodium sulfate and evaporated and the resulting residue is chromatographed on silica gel (2–3% MeOH in chloroform with 0.1% ammonia) to obtain BOC-Lys (Z) [ΨCH$_2$NH]Lys (BOC)-Pro-Trp-Tle-Leu-OEt (Seq ID No: 5) as a white foam (0.93 g). FABMS M+1 1132

Step B: Preparation of Lys[ΨCH$_2$NH]Lys-pro-Trp-Tle-Leu-OEt (Seq ID No: 5)

BOC-Lys(Z)[ΨCH$_2$NH] Lys(BOC)-Pro-Trp-Tle-Leu-OEt (Seq ID No: 5) (0.90 g, 0.8 mmol) is dissolved in 60 mL of ethanol, treated with 0.05 g of 20% palladium on carbon, and placed under 50 psi of hydrogen. After 22 hours the reaction is filtered and the solvent is removed under reduced pressure. This material is treated with a solution of 23 mL TFA, 1 mL water, 0.5 mL anisole, 1.2 mL thioanisole, and 0.5 mL ethane dithiol, and stirred at room temperature for 6.5 hours. The reaction is poured into 400 mL of diethyl ether and allowed to stand overnight and the resulting precipitate is filtered and dried under vacuum. The resulting crude solid is purified by preparative HPLC (C-18, 20–50% acetonitrile in water with 0.1% TFA) to obtain Lys[ΨCH$_2$NH]Lys-Pro-Trp-Tle-Leu-OEt (Seq ID No: 5) (0.31 g). FABMS M+1 798

EXAMPLE 4

Lys [ΨCH$_2$NH]Lys-Pro-Trp-Tle-Leu (L-Leucine, N-[N-[N-[1-[N$^2$-(2 6-diaminohexyl)-L-lysyl]-L-prolyl]0L-tryptophyl]-3-methyl-L-valyl]-,(S)-, trifluroacetate (1:3) (salt)) (Seq ID No: 5)

Lys [ΨCH$_2$NH]Lys-Pro-Trp-Tle-Leu-OEt (Seq ID No: 5) (Example 3) (0.56 g, 0.49 mmol) is dissolved in 3 mL of water, treated with 1.0 mL of a 2N solution of sodium hydroxide, and stirred at room temperature for 2 hours. The reaction is neutralized with HCl and the water is removed under reduced pressure. The resulting crude solid is purified by preparative HPLC (C-18, 20–50% acetonitrile in water with 0.1% TFA) to obtain Lys[ΨCH$_2$NH]Lys-Pro-Trp-Tle-Leu (Seq ID No: 5) (0.11 g). FABMS M+1 770

The following compound is prepared using methodology described in Example 3:

EXAMPLE 5

H$_2$N(CH$_2$)$_6$[ΨCH$_2$NH]Lys-Pro-Trp-Tle-Leu-OEt (Seq ID No: 6) FABMS M+1 783.

The following compound is prepared using methodology described in Example 4:

EXAMPLE 6

H$_2$N, (CH$_2$)$_6$[ΨCH$_2$NH]Lys-Pro-Trp-Tle-Leu (Seq ID No: 6) FABMS M+1 755.

EXAMPLE 7

BAP-PRO-Trp-Tle-Leu-OEt (Leucine, N-[N-[N-[1-[Bis(3-aminopropyl)acetyl]-L-prolyl]-L-tryptophyl]-3-methyl-L-valyl]-,ethyl ester, (S)- (Seq ID No: 7)

Step A: Preparation of di-tert-butyl Bis(3-phthalimidopropyl)malonate

Sodium hydride (4.08 g, 102 mmol, 60% by weight) is washed with hexanes and mixed with 30 mL of THF. The mixture is cooled to 0° C. and treated with a solution of di-tert-butyl malonate (10.0 g, 46.23 mmol) and N-(3-bromopropyl)phthalimide (24.7 g, 92.46 mmol) in 80 mL of THF. After the addition the reaction is allowed to stir at room temperature for 2 hours and then is heated to reflux overnight. The reaction is cooled and the volatiles are removed under reduced pressure. The residue is partitioned between water and chloroform. The organic layer is dried with Na$_2$SO$_4$ and the solvents are removed under reduced pressure. The resulting product is recrystallized from hexane-ethyl acetate to give 19.66 g of di-tert-butyl bis(3-phthalimidopropyl)-malonate as a white solid.

Step B: Preparation of Bis(3-phthalimidopropyl)acetic acid

A mixture of di-tert-butyl Bis(3-phthalimidopropyl)-malonate (Step A) (6 g, 10.16 mmol), a catalytic amount of PTSA in 60 mL of toluene is heated to reflux for 4 hours. The reaction is cooled and a solid is filtered and dried. The solid is heated neat (under a nitrogen atmosphere) for 2 hours. From this procedure 3.81 g of Bis(3-phthalimidopropyl)acetic acid is isolated.

Step C: Preparation of 1-[Bis(3-phthalimidopropyl)-acetyl]-Proline tert-Butyl Ester Bis(3-phthalimidopropyl)acetic acid (Step B) (2.5 g, 5.5 mmol), proline tert-butyl ester hydrochloride (0.42 g, 2.0 mmol), and N-methylmorpholine (1.19 g, 5.4 mmol) in 7 mL of DMF are cooled to 0° C. and treated with TBTU (0.64 g, 2.0 mmol). The mixture is then stirred at room temperature for 18 hours. The reaction mixture is poured into 70 mL of saturated sodium bicarbonate solution and extracted with two 50 mL portions of ethyl acetate. The combined organics are washed with 1 M KHSO$_4$, saturated aqueous bicarbonate and brine, and dried over Na2SO$_4$. The volatiles are removed under reduced pressure and the residue is chromatographed over silica gel (4:1 chloroform, ethyl acetate eluent) to give 2.88 g of 1-[Bis(3-phthalimidopropyl)acetyl]-proline tert-butyl ester.

Step D: Preparation of 1-[Bis(3[N-benzyloxycarbonylamino]propyl)acetyl-proline tert-Butyl Ester 1- [Bis (3-phthal imidopropyl)acetyl]-proline tert-butyl ester (Step C) (2.88 g, 4.90 mmol) and hydrazine hydrate (0.54 g, 10.78 mmol) are heated to reflux in 20 mL of ethanol for 1.5 hours. The reaction mixture is cooled, filtered, and the filtrate is evaporated under reduced pressure. The resulting residue is treated with 30 mL of 6% aqueous sodium carbonate and THF containing ZOSu (2.68 g, 10.78 mmol). The reaction is stirred at room temperature for 15 hours, the THF is removed under reduced pressure, and the remaining mixture is extracted with chloroform and the organic extract is dried with sodium sulfate and evaporated under reduced pressure. The resulting residue is chromatographed over silica gel (4:1 chloroform ethyl acetate eluent) to give 1.09 g of 1-[Bis(3[N-benzyloxycarbonylamino]propyl)acetyl]proline tert-butyl ester as a clear oil.

Step E: Preparation of
1-[Bis(3[N-benzyloxycarbonyl-amino]propyl)acetyl]-Pro-Trp-Tle-Leu-OEt (Seq ID No: 7)

1- [Bis ( 3 [N-benzyloxycarbonylamino]propyl)- 1-acetyl]-proline tert-butyl ester (Step D) (0.53 g, 0.89 mmol) is dissolved in 7.5 mL of methylene chloride and treated with 5.5 mL of trifluoroacetic acid. The reaction is stirred at room temperature for 1.5 hours and the volatiles are removed under reduced pressure. The residue is dissolved with 16 mL of 0.4N NaOH and extracted with diethyl ether. The aqueous phase is adjusted to pH 5 with 1N HCl and extracted with ethyl acetate. The organic extract is dried with brine and sodium sulfate and the volatiles are removed under reduced pressure. The resulting acid (0.37 g, 0.69 mmol) is dissolved in 5 mL of DMF along with the tripeptide ester Trp-Tle-Leu-OEt (0.32 g, 0.69 mmol) and N-methylmorpholine (0.37 mL, 1.4 mmol). After cooling the solution to 0° C., TBTU (0.24 g, 0.75 mmol) is added. The reaction is stirred at 0° C. for 10 minutes then for 15 hours at room temperature. The reaction mixture is poured into 70 mL of saturated aqueous sodium bicarbonate solution and extracted with ethyl acetate. The organic extract is washed with in KHSO4, saturated bicarbonate solution, water, brine, and dried over Na2SO4. The solvents are evaporated under reduced pressure and the resulting residue chromatographed over silica gel (2% methanol 0.1% ammonia in chloroform) to give 0.65 g of 1-[Bis (3[N-benzyloxycarbonylamino]propyl)acetyl]-Pro-Trp-Tle-Leu-OEt (Seq ID No: 7) as a white solid.

Step F: Preparation of BAP-Pro-Trp-Tle-Leu-OEt (Seq ID No: 7)

A solution of 1-[Bis (3[N-benzyloxycarbonylamino]propyl) acetyl]-Pro-Trp-Tle-Leu-OEt (Seq ID No: 7) (Step E) (0.43 g, 0.48 mmol) in 75 mL of ethanol is treated with 0.1 g 20% palladium on carbon and placed under 44 pounds per square inch (psi) of hydrogen for 2 hours. The catalyst is removed by filtration and the filtrate is evaporated to give 0.31 g of BAP-Pro-Trp-Tle-Leu-OEt (Seq ID No: 7); Electrospray Mass Spectrometry (ESMS) 711 (M+)

EXAMPLE 8

BAP-Pro-Trp-Tle-Leu (L-Leucine, N-[N-[N-[1-[Bis (3-aminopropyl)acetyl]-L-prolyl]-L-tryptophyl]-3-methyl-L-valyl]-,(S)-,trifluoroacetate (1:2) salt) (Seq ID No: 7)

BAP-Pro-Trp-Tle-Leu-OEt (Seq ID No: 7) (Example 7) (0.31 g, 0.42 mmol) is dissolved in 3 mL of ethanol and treated with 1 mL of 2 M NaOH. The solution is stirred at room temperature for 2 hours. The reaction is neutralized with aqueous HCl and evaporated. The residue is subjected to preparative HPLC (C-18, 10–50% acetonitrile in water with 0.1% TFA) which is lyophilized to afford 280 mg of BAP-Pro-Trp-Tle-Leu (Seq ID No: 7) as a trifluoroacetate salt; ESMS 683 (M+)

The following compound is prepared using methodology described in Example 7.

EXAMPLE 9

BAB-Pro-Trp-Tle-Leu-OEt (L-Leucine, N-[N-[N-[1-[Bis(4-aminobutyl)acetyl]-L-prolyl]-L-tryptophyl]-3-methyl-L-valyl]-,ethyl ester,(S)-) (Seq ID No: 7)

Example 9 is prepared in a manner analogous to Example 7; ESMS 739 (M+)

The following compound is prepared using methodology described in Example 8.

EXAMPLE 10

BAB-Pro-Trp-Tle-Leu-OH (L-Leucine, N-[N-[N-[1-[Bis (4-aminobutyl)acetyl]-L-prolyl]-L-tryptophyl]-3-methyl-L-valyl]-, (S)- ,trifluoroacetate (1:2) salt) (Seq ID No: 7); ESMS 711 (M+)

EXAMPLE 11

BGP-Pro-Trp-Tle-Leu (L-Leucine, N-[N-[N-[1-[Bis (3-guanidinylpropyl)acetyl]-L-prolyl]-L-tryptophyl]-3-methyl-L-valyl]-,ethyl ester, (S)- (Seq ID No: 7)

Step A: Preparation of
1-[Bis(3[N,N'dibenzyloxycarbonylguanidino]propyl)-1-acetyl]-proline tert-Butyl Ester A solution of 1-[Bis(3 [N-benzyloxycarbonylamino]-propyl)-1-acetyl]-proline tert-butyl ester (0.38 g, 0.63 mmol) in 75 mL of ethanol is treated with 0.1 g of 20% palladium on carbon and placed under 44 psi of hydrogen for 2 hours. The catalyst is removed by filtration and the filtrate is evaporated to give an oily residue. This is dissolved in 6 mL of DMF and treated with N,N-Bis (benzyloxycarbonyl)-S-methyl thiourea (0.648 g, 1.81 mmol), and triethyl amine (0.22 mL, 1.65 mmol). After stirring at room temperature for 65 hours, the DMF is removed under reduced pressure and the residue is partitioned between ethyl acetate and saturated sodium bicarbonate solution. The organic layer is washed with brine, dried over Na2SO4, and the solvent is evaporated under reduced pressure. The residue is chromatographed over silica gel (5:1 chloroform, ethyl acetate) to afford 0.5 g of 1-[Bis (3[N,N'dibenzyloxycarbonylguanidino]-propyl) acetyl]-proline tert-Butyl Ester.

Step B; Preparation of
1-[Bis(3[N,N'dibenzyloxycarbonylguanidino]propyl)acetyl]-Pro-Trp-Tle-Leu-OEt (Seq ID No: 7)

In a manner analogous to Example 1 Step E, 1-[Bis(3[N,N'dibenzyloxycarbonylguanidino]propyl)-acetyl]-proline tert-Butyl Ester (0.33 g, 0.37 mmol) is converted to 0.36 g of 1- [Bis(3 [N,N'dibenzyloxycarbonylguanidino]propyl)acetyl]-Pro-Trp-Tle-Leu-OEt (Seq ID No: 7).

Step C: BGP-Pro-Trp-Tle-Leu-OEt (Seq ID No: 7)

This compound is prepared using methodology described in Example 7 Step F; ESMS 795 (M+)

The following compound is prepared using methodology described in Example 8.

EXAMPLE 12

BGP-Pro-Trp-Tle-Leu (L-Leucine, N-[N-[N-[1-[Bis(3-guanadinylpropyl)acetyl]-L-prolyl]-L-tryptophyl]-3-methyl-L-valyl]-, (S)-, 1:3 trifluoroacetate) (Seq ID No: 7); ESMS 767 (M+).

---

We claim:

1. A compound of Formula I $$R-CH-CH_2-X-CH-\overset{O}{\underset{\|}{C}}-Pro-Trp-Tle-Leu-OR^3$$
$$\underset{R^1}{\overset{|}{(CH_2)_n}} \quad \underset{\underset{R^2}{\overset{|}{(CH_2)_{n^1}}}}{\overset{|}{\underset{|}{CH_2}}\underset{|}{\overset{|}{CH_2}}\underset{|}{\overset{|}{CH_2}}}$$

(Seq ID No: 3)

wherein

R is H or $NH_2$;

$R^1$ and $R^2$ are each independently $NH_2$ or $$-NH-\overset{NH}{\underset{\|}{C}}-NH_2;$$

$R^3$ is H or lower alkyl;

n is zero or an integer of one to four;

$n^1$ is zero or one;

X is NH or $CH_2$; provided:

when R is H and X is $CH_2$ then $R^1$ and $R^2$ are $NH_2$ or $$-NH-\overset{O}{\underset{\|}{C}}-NH_2,$$

n is zero or an integer of one to four and $n^1$ is zero or one;

when R is $NH_2$ and X is $CH_2$ then $R^1$ is $NH_2$ or $$-NH-\overset{NH}{\underset{\|}{C}}-NH_2,$$

$R^2$ is $NH_2$, n is three or four, and $n^1$ is zero or one;

when R is H and X is NH then $R^1$ is $NH_2$, $R^2$ is $NH_2$ or $$-NH-\overset{NH}{\underset{\|}{C}}-NH_2,$$

n is zero or an integer of one to four and $n^1$ is zero or one;

further provided when R is $NH_2$ then X is not NH; and corresponding optical isomers thereof or a pharmaceutically acceptable salt thereof.

2. A compound according to claim 1 in which X is NH.

3. A compound according to claim 1 selected from the group consisting of:
 $H_2N(CH_2)_6$ [ΨCH$_2$NH]Lys-Pro-Trp-Tle-Leu-OEt (Seq ID No: 6);
 $H_6N(CH_2)_6$ [ΨCH$_2$NH]Lys-Pro-Trp-Tle-Leu (Seq ID No: 6);
 BAP-Pro-Trp-Tle-Leu-OEt (Seq ID No: 7);
 BAP-Pro-Trp-Tle-Leu (Seq ID No: 7);
 BAB-Pro-Trp-Tle-Leu-OEt (Seq ID No: 7);
 BAB-Pro-Trp-Tle-Leu (Seq ID No: 7);
 BGP-Pro-Trp-Tle-Leu-OEt (Seq ID No: 7); and
 BGP-Pro-Trp-Tle-Leu (Seq ID No: 7).

4. A method of treating schizophrenia in a host comprising administering to a host suffering therefrom a therapeutic effective amount of a compound according to claim 1 in unit dosage form.

5. A pharmaceutical composition adapted for administration as an agent for treating schizophrenia comprising a therapeutic effective amount of a compound according to claim 1 in admixture with a pharmaceutically acceptable excipient, diluent, or carrier.

6. A pharmaceutical composition adapted for administration as an analgesic agent comprising a therapeutic effective amount of a compound according to claim 1 in admixture with a pharmaceutically acceptable excipient, diluent, or carrier.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Xaa Xaa Xaa Xaa Xaa Xaa
        1                   5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="$CH_2NH$ - Bond
            replaces CONH bond"

( x i ) SEQUENCE DESCRIPTION: SEQ ID NO:2:

Lys Lys Pro Tyr Ile Leu
        1                   5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="$CH_2X$ - Bond
            replaces CONH bond wherein X is NH or $CH_2$"

( x i ) SEQUENCE DESCRIPTION: SEQ ID NO:3:

Xaa Xaa Pro Trp Xaa Leu
        1                   5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site ( B ) LOCATION: 1..2
( D ) OTHER INFORMATION: /note="CH₂NH - bond replaces CONH bond"

( x i ) SEQUENCE DESCRIPTION: SEQ ID NO:4:

Arg  Lys  Pro  Trp  Xaa  Leu
1                    5

( 2 ) INFORMATION FOR SEQ ID NO:5:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1..2
    ( D ) OTHER INFORMATION: /note="CH₂NH - bond replaces CONH bond"

( x i ) SEQUENCE DESCRIPTION: SEQ ID NO:5:

Lys  Lys  Pro  Trp  Xaa  Leu
1                    5

( 2 ) INFORMATION FOR SEQ ID NO:6:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:6:

Lys  Pro  Trp  Xaa  Leu
1                5

( 2 ) INFORMATION FOR SEQ ID NO:7:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

Pro  Trp  Xaa  Leu
1

( 2 ) INFORMATION FOR SEQ ID NO:8:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:8:

Xaa  Pro  Trp  Xaa  Leu
1                5

( 2 ) INFORMATION FOR SEQ ID NO:9:

(i) SEQUENCE CHARACTERISTICS:
 (A) LENGTH: 5 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:9:

```
Lys  Pro  Trp  Xaa  Leu
 1                    5
```